US00PP36447P2

(12) United States Plant Patent
Cong et al.

(10) Patent No.: US PP36,447 P2
(45) Date of Patent: Feb. 11, 2025

(54) ***HEDYCHIUM* PLANT NAMED 'FAIRY GIRL'**

(50) Latin Name: ***Hedychium coronarium* x *simaoense***
Varietal Denomination: FAIRY GIRL

(71) Applicants: Guangzhou Landscape Architecture Co., Ltd, Guangzhou (CN); Foshan Lianyi Biotechnology Co., Ltd, Foshan (CN)

(72) Inventors: Tang Cong, Guangzhou (CN); Lin Ling, Guangzhou (CN); Zhang Bin, Guangzhou (CN); Liu Wenyi, Guangzhou (CN); Luo Shishu, Guangzhou (CN); Liu Nian, Guangzhou (CN)

(73) Assignees: Guangzhou Landscape Architecture Co., Ltd (CN); Foshan Lianyi Biotechnology Co., Ltc. (CN)

( * ) Notice: Subject to any disclaimer, the term of this patent is extended or adjusted under 35 U.S.C. 154(b) by 0 days.

(21) Appl. No.: 18/416,211

(22) Filed: Jan. 18, 2024

(51) Int. Cl.
*A01H 5/02* (2018.01)
*A01H 6/00* (2018.01)

(52) U.S. Cl.
USPC ..... Plt./263.1

(58) Field of Classification Search
USPC ..... Plt./373, 263.1
CPC ..... A01H 5/02; A01H 5/00; A01H 6/00
See application file for complete search history.

(56) References Cited

U.S. PATENT DOCUMENTS

PP34,346 P2 * 6/2022 Chen ..... Plt./373

* cited by examiner

*Primary Examiner* — June Hwu

(57) ABSTRACT

A new and distinct cultivar of *Hedychium* plant named 'FAIRY GIRL' is disclosed characterized by robust plants with resistance to *Pyricularia zingiberi* (Ginger Blast). Inflorescences are dense and composed of attractive pale pink flowers with orange-red anthers. The new variety is useful as an ornamental plant in warm, wet climates.

2 Drawing Sheets

Latin name of the genus and species: *Hedychium coronarium* x *simaoense*.

Variety denomination: 'FAIRY GIRL'.

BACKGROUND OF THE INVENTION

The new cultivar, *Hedychium* 'FAIRY GIRL', is the product of a planned breeding program. The intent of the breeding program was to produce new ornamental ginger varieties for landscape purposes with improved resistance to diseases and pests in hot, wet climates. The new variety originated from a cross pollination of the seed parent, an unnamed, unpatented variety of *Hedychium coronarium*, with the pollen parent, an unnamed, unpatented variety of *Hedychium simaoense*. The cross pollination was made during March of 2004 in Guangzhou, China, at a research nursery. The new cultivar 'FAIRY GIRL' was selected in December of 2007 at the same location.

Asexual reproduction of the new cultivar 'FAIRY GIRL' was first performed by division in Guangzhou, China, at a research nursery May of 2008. *Hedychium* 'FAIRY GIRL' has since produced multiple generations and has shown that the unique features of this cultivar are stable and reproduced true to type.

SUMMARY OF THE INVENTION

The cultivar 'FAIRY GIRL' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'FAIRY GIRL'. These characteristics in combination distinguish 'FAIRY GIRL' as a new and distinct *Hedychium* cultivar:

1. Usefulness as landscape plant in warm and wet climates.
2. Strong plants resistant to *Pyricularia zingiberi* (ginger blast).
3. Ornamental flowers of pale pink with orange-red anthers.
4. Abundant inflorescence production.

PARENTAL COMPARISONS

Plants of the new cultivar 'FAIRY GIRL' are similar to plants of the seed parent in most horticultural characteristics. However, plants of the new cultivar 'FAIRY GIRL' differ in the following:

1. Plants of the new cultivar produce more inflorescences than plants of the seed parent.
2. Inflorescences of the new cultivar are both longer and wider than inflorescences of the seed parent.
3. In the new cultivar, the lateral staminodes are obovate; in the seed parent oblanceolate.

Plants of the new cultivar 'FAIRY GIRL' are similar to the pollen parent in most horticultural characteristics. However, plants of the new cultivar 'FAIRY GIRL' differ in the following:

1. In the new cultivar, the-lateral staminodes are obovate; in the pollen parent oblong.
2. The curl of the corolla lobes in the new cultivar is obvious; in the pollen parent inconspicuous.

3. In the new cultivar the filament color is light pink; in the pollen parent darker purple-red.

COMMERCIAL COMPARISON

The new cultivar 'FAIRY GIRL' can be compared to the unnamed, unpatented variety of *Hedychium coronarium* found in the trade. Plants of the new cultivar 'FAIRY GIRL' differ in the following:

1. Plants of *Hedychium* 'FAIRY GIRL' are taller than plants of *Hedychium coronarium.*
2. Individual flowers of *Hedychium* 'FAIRY GIRL' are longer than flowers of *Hedychium coronarium.*
3. Flower color of the new variety is a brighter orange-yellow than flower color of *Hedychium coronarium.*
4. The new variety has a 50% higher uniformity of flowering than *Hedychium coronarium.*

BRIEF DESCRIPTION OF THE PHOTOGRAPHS

The accompanying photographs illustrate in full color typical plants of 'FAIRY GIRL' grown outdoors, in the ground in Guangzhou, China. The photographs were taken using conventional techniques and equipment. While the colors in these photographs may display variances of color as compared to the living cultivar, due to LRV (light reflectance value), they are as accurate as possible using conventional photographic techniques. Colors in the photographs may appear to differ slightly from the color values cited in the botanical description, which accurately describe the colors of the new *Hedychium* plant. Temperatures ranged from approximately 18° to 30° C., night and day. No artificial light, photoperiodic treatments or chemical treatments were given to the plants.

DETAILED BOTANICAL DESCRIPTION

Figure 1:
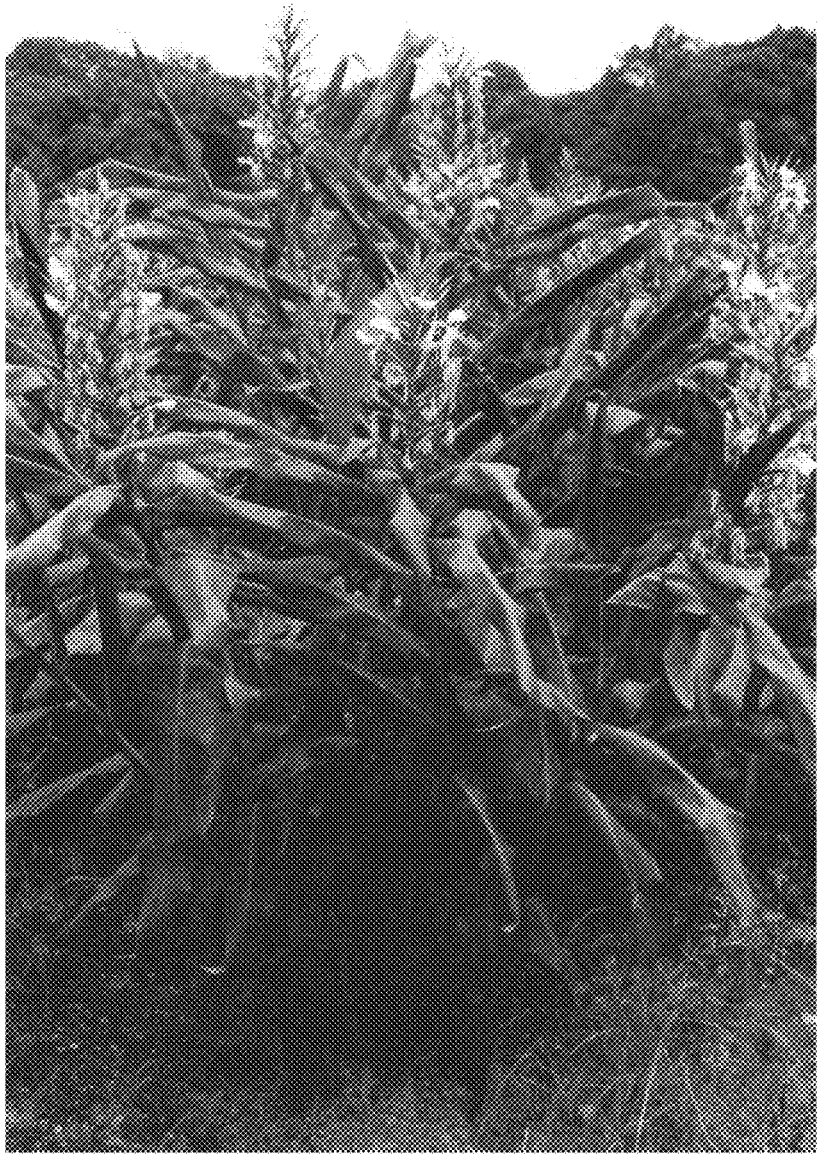
FIG. 1 illustrates in full color typical of plants of *Hedychium* 'FAIRY GIRL' in the ground at approximately 18 months.
Figure 2:
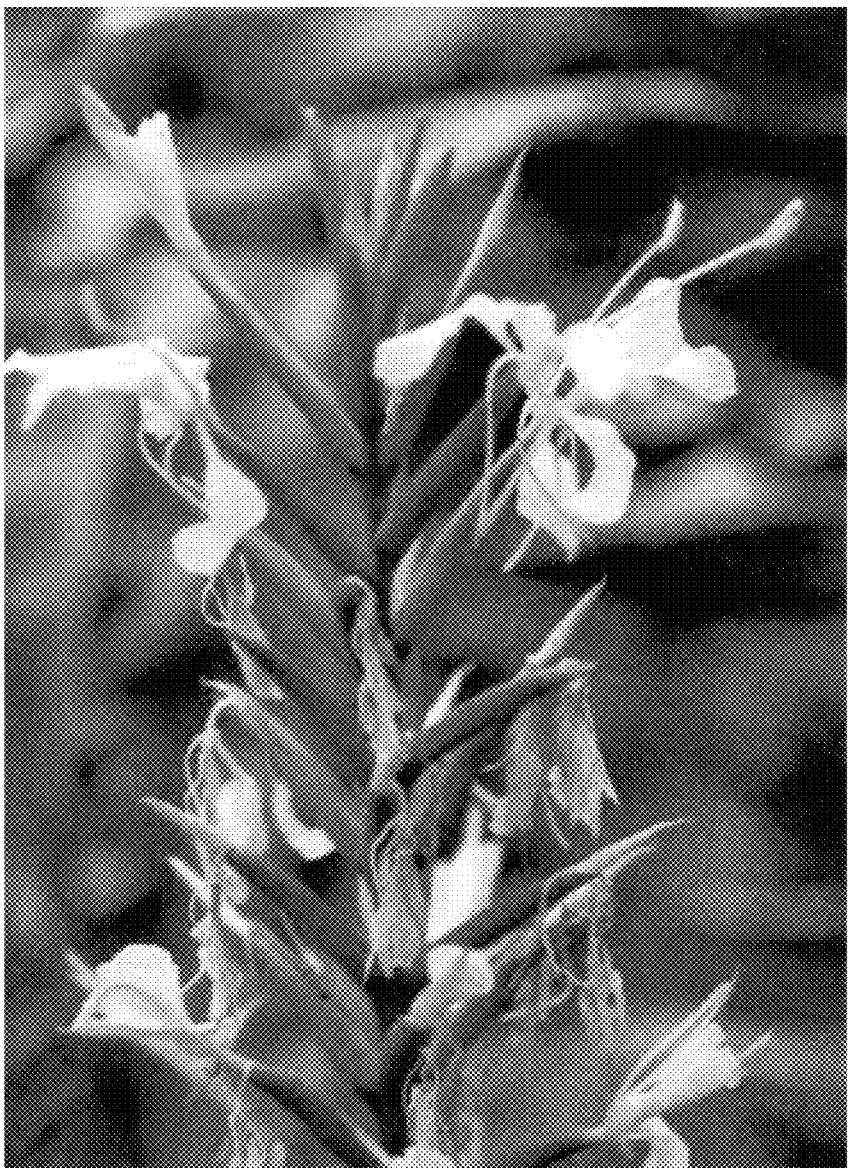
FIG. 2 illustrates in full color a typical inflorescence of *Hedychium* 'FAIRY GIRL'.

In the following description, color references are made to The Royal Horticultural Society Colour Chart, 2019 (reprint 6$^{th}$ edition), except where general terms of ordinary dictionary significance are used. The following observations and measurements describe 'FAIRY GIRL' plants in a field in Guangzhou, China. Average day temperature was around 25° to 30° C.; average night temperature was around 18° to 25° C. No artificial light, photoperiodic treatments or chemical treatments were given to the plants. Natural light conditions were full sunlight. Measurements and numerical values represent averages of typical plant types.

Botanical classification: *Hedychium coronarium simaoense* 'FAIRY GIRL'.

PROPAGATION

Type of propagation typically used: Division from side shoots.

Time to rooting: About 7 days at temperatures above 15° C.

Root description: Cylindrical rhizomes. 33.8 cm long, 5.7 cm in diameter. Fleshy, colored RHS White 155D.

PLANT

Age of plant described: Approximately 9 months.
Container size of the plant described: Field cultivation.
Plant type: Perennial evergreen.
Growth habit: Columnar, erect.
Height: 165 to 190 cm to top of foliar plane; 160 to 180 cm to top of floral plane.
Plant spread: 50 to 70 cm.
Growth rate: Moderate.
Vigor: High.
Branching characteristics: No branching, pinching required.
Internode length: 7 to 11 cm.
Pseudostem:
- *Shape.*—Cylindrical.
- *Aspect.*—20° to 60° from vertical.
- *Strength.*—Moderate.
- *Pubescence.*—None.
- *Luster.*—Semi-glossy.
- *Color.*—Developing: RHS Yellow-Green 146D. At Internodes: RHS Yellow-Green 154D. Developed: RHS Yellow-Green 146A.
- *Other.*—Herbacious, pseudostem.

FOLIAGE

Leaf:
- *Arrangement.*—Alternate phyllotaxy.
- *Average length.*—55 cm.
- *Average width.*—12 cm.
- *Shape of blade.*—Lanceolate.
- *Apex.*—Tapered.
- *Base.*—Cuneate.
- *Margin.*—Weak undulate.
- *Texture.*—Thinly leathery, both surfaces.
- *Luster.*—Upper side: Glossy. Under side: Semi-glossy.
- *Rugosity.*—Smooth, both sides.
- *Color.*—Young foliage upper side: RHS Green 137C. Young foliage, under side: RHS Yellow-Green 146B. Mature foliage upper side: RHS Yellow-Green 146A. Mature foliage, under side: RHS Yellow-Green 148D. Fall foliage, upper side: RHS Green 137D. Fall foliage, under side: RHS Yellow-Green 146B.

Venation:
- *Type.*—Pinnate.
- *Color, upper side.*—RHS Green 137D.
- *Color, under side.*—RHS Yellow-Green 146B.

Ligule:
- *Length.*—Average range 2 to 4 cm.
- *Width.*—8 mm.
- *Texture.*—Glabrous.
- *Color.*—RHS Yellow-Green 146A.

Sheath:
- *Length.*—Average range 3 to 5 cm.
- *Width.*—1 cm.
- *Color.*—RHS Yellow-Green 146D.

Petiole:
- *Average length.*—0.3 cm.
- *Average diameter.*—0.5 cm.
- *Color.*—Upper surface: RHS Yellow-Green 146A. Lower surface: RHS Yellow-Green 148D.
- *Texture.*—Leathery.

*Luster*.—Matte.
*Strength*.—High.

FLOWER

Natural flowering season: June to October.
Inflorescence:
*Type and habit*.—Terminal spike. Pagoda-shaped cylinder.
*Height*.—36 cm.
*Width*.—17 cm.
Flower:
*Aspect*.—Upright.
*Habit*.—Freely.
*Quantity*.—40 to 50 per inflorescence. 5 to 10 inflorescences per plant at one time.
*Longevity as a cut flower*.—1 to 2 days.
*Longevity on plant*.—3 days.
*Length*.—8 to 9 cm.
*Diameter*.—4 to 5 cm.
*Tube diameter*.—0.2 cm.
*Tube length*.—4.2 cm.
*Tube texture*.—Fleshy.
*Throat diameter*.—0.2 cm.
*Throat texture*.—Fleshy.
*Corolla throat color*.—RHS Red-Purple 62B; venation Red-Purple 62B.
*Corolla tube color*.—RHS Red-Purple 62B; venation Red-Purple 62B.
Bud:
*Length*.—2 to 5 cm.
*Diameter*.—0.2 to 0.3 cm.
*Shape*.—Cylindrical, apex acuminate.
*Texture*.—Fleshy.
*Luster*.—Matte.
*Color*.—RHS Yellow-Green 142C.
Petals:
*Arrangement*.—Three lobed petals consisting of Two lateral staminodes and one labellum.
Labellum:
*Quantity*.—1.
*Length*.—3.4 cm.
*Width*.—3.6 cm.
*Shape*.—Oblate oval.
*Tip*.—Cleft. Depth around 5 to 8 mm.
*Base*.—Attenuate.
*Claw length*.—About 8 mm.
*Margin*.—Entire; low undulation.
*Texture*.—Fleshy, both sides.
*Appearance*.—Upper side: Matte. Underside: Semi-glossy.
*Luster*.—None.
*Color*.—When opening: Upper side: RHS Yellow 2D. Under side: RHS Yellow 2D. Fully opened: Upper side: RHS Red-Purple 62C. Under side: RHS Red-Purple 62C. Venation: RHS Red-Purple 62C. Fading: Upper side: RHS Brown N200B. Under side: RHS Brown N200B.
Lateral staminoides:
*Arrangement*.—Opposite; one pair.
*Quantity*.—2.
*Length*.—3.2 cm.
*Width*.—1.8 cm.
*Shape*.—Obovate.
*Margin*.—Entire.
*Apex*.—Obtuse.
*Base*.—Truncate.
*Texture*.—Glabrous both surfaces.
*Color*.—When opening: Upper surface: RHS Yellow 10D. Under surface: RHS Yellow 10D. Fully opened: Upper surface: RHS Yellow 10D. Under surface: RHS Yellow 10D. Venation: RHS Yellow 10D. Fading: Upper surface: RHS Brown N200B. Under surface: RHS Brown N200B.
Corolla lobes:
*Arrangement*.—Opposite; one whorl pair.
*Quantity*.—1 dorsal, 2 lateral.
*Length*.—Average 3.0 cm.
*Width*.—Dorsal: 1.3 cm. Lateral: 8 mm.
*Shape*.—Linear.
*Margin*.—Entire.
*Apex*.—Obtuse.
*Base*.—Truncate.
*Aspect*.—Conspicuously curled.
*Texture*.—Glabrous, both surfaces.
*Color*.—When opening: Upper surface: RHS Yellow 10D. Under surface: RHS Yellow 10D. Fully opened: Upper surface: RHS Yellow 10D. Under surface: RHS Yellow 10D. Venation: RHS Yellow 10D. Fading: Upper surface: RHS Brown N200B. Under surface: RHS Brown N200B.
Calyx:
*Length*.—3.3 cm.
*Width*.—0.3 cm.
*Shape*.—Long tubular.
Sepals:
*Quantity*.—1.
*Number of whorls*.—1.
*Length*.—3.3 cm.
*Width*.—0.3 cm.
*Shape*.—Long tubular.
*Apex*.—Gradually tapering.
*Base*.—Even, fused.
*Margin*.—Entire.
*Texture*.—Fleshy, all surfaces.
*Color*.—When opening: Upper surface: RHS Yellow-Green 145C. Under surface: RHS Yellow-Green 145C. Fully opened: Upper surface: RHS Yellow-Green 145C. Under surface: RHS Yellow-Green 145C.
Peduncle:
*Terminal length*.—4.5 cm.
*Terminal diameter*.—1.3 cm.
*Aspect*.—0° from lateral branch axis.
*Strength*.—Low.
*Texture*.—Leathery.
*Luster*.—Matte.
*Color*.—RHS Yellow-Green 145C.
Pedicels:
*Length*.—0.4 cm
*Width*.—0.2 cm.
*Strength*.—Low.
*Texture*.—Leathery.
*Luster*.—Matte.
*Color*.—RHS Yellow 18C.
*Angle*.—0° from peduncle axis.
Floral bracts:
*Length*.—5.1 cm.
*Width*.—1 cm.

*Shape*.—Strongly furled, lanceolate when manually unfurled.
*Texture*.—Leathery.
*Color*.—RHS Yellow-Green 144A.
*Quantity*.—2 per individual flower.

Bracteole:
*Length*.—2.3 cm
*Width*.—6 mm.
*Shape*.—Linear.
*Texture*.—Leathery.
*Color*.—RHS Yellow-Green 144B.
*Quantity*.—1 per individual flower.

Floral fragrance: Faint sweet fragrance.

REPRODUCTIVE ORGANS

Stamens: (androecium).
*Number*.—1 per flower.
*Filament length*.—4 cm.
*Filament color*.—RHS Red 37C.
*Anther length*.—1.1 cm.
*Anther width*.—0.3 cm.
*Anther color*.—RHS Orange-Red N30A.
*Anther shape*.—Oblong.
*Pollen color*.—RHS Yellow 16D.
*Pollen quantity*.—Moderate.

Pistil: (gynoecium).
*Number*.—1 per flower.
*Length*.—1.1 cm.
*Stigma shape*.—Spherical.
*Stigma color*.—RHS Yellow 21A.

OTHER CHARACTERISTICS

Fruits and seeds: Not observed.

Temperature tolerance: Tolerates temperatures from approximately 0° C. to 40° C. High tolerance to wind and rain.

Disease/pest resistance: Observed resistance to Ginger blast (*Pyricularia zingiberi*). Neither resistance nor susceptibility to other normal diseases *Hedychium* observed. Neither resistance nor susceptibility to normal pests of *Hedychium* observed.

What is claimed is:

1. A new and distinct cultivar of *Hedychium* plant named 'FAIRY GIRL' as herein illustrated and described.

* * * * *